(12) United States Patent
Lee et al.

(10) Patent No.: US 9,999,397 B2
(45) Date of Patent: Jun. 19, 2018

(54) BIOSIGNAL PROCESSING METHOD AND APPARATUS

(71) Applicant: Samsung Electronics Co., Ltd., Suwon-si (KR)

(72) Inventors: TakHyung Lee, Suwon-si (KR); JongPal Kim, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 154 days.

(21) Appl. No.: 14/812,441

(22) Filed: Jul. 29, 2015

(65) Prior Publication Data

US 2016/0183884 A1 Jun. 30, 2016

(30) Foreign Application Priority Data

Dec. 29, 2014 (KR) .................. 10-2014-0192674

(51) Int. Cl.
*A61B 5/02* (2006.01)
*A61B 5/00* (2006.01)
*A61B 5/0428* (2006.01)

(52) U.S. Cl.
CPC ........ *A61B 5/7225* (2013.01); *A61B 5/04288* (2013.01)

(58) Field of Classification Search
CPC .................. A61B 5/04288; A61B 5/7225
See application file for complete search history.

(56) References Cited

U.S. PATENT DOCUMENTS

| 6,602,201 | B1 * | 8/2003 | Hepp ................. A61B 5/02028 |
| | | | 600/526 |
| 8,461,744 | B2 * | 6/2013 | Wiener ......... A61B 17/320092 |
| | | | 310/323.01 |
| 8,594,779 | B2 * | 11/2013 | Denison ............... A61B 5/0478 |
| | | | 600/544 |
| 8,624,871 | B2 | 1/2014 | Nihei et al. |
| 8,892,198 | B2 * | 11/2014 | Bohorquez .......... A61B 5/0537 |
| | | | 600/547 |
| 2006/0224073 | A1 | 10/2006 | Lin et al. |
| 2013/0090567 | A1 * | 4/2013 | Lee ........................ A61B 7/003 |
| | | | 600/529 |
| 2013/0197510 | A1 * | 8/2013 | Heckel ............... A61B 18/1206 |
| | | | 606/41 |
| 2014/0111444 | A1 | 4/2014 | Lindfors et al. |
| 2014/0213880 | A1 | 7/2014 | Banet et al. |

FOREIGN PATENT DOCUMENTS

| JP | 5368295 B2 | 9/2013 |
| JP | 2013-254456 A | 12/2013 |
| KR | 10-2009-0046744 A | 5/2009 |
| KR | 10-1385650 B1 | 4/2014 |

* cited by examiner

*Primary Examiner* — George Manuel
(74) *Attorney, Agent, or Firm* — NSIP Law

(57) ABSTRACT

A biosignal processing apparatus and method thereof include a signal receiver and a signal processor. The signal receiver is configured to receive a biosignal having a corresponding electrical physical quantity from a sensor. The signal processor includes a voltage inputter and a current inputter, and configured to process the biosignal using one of the voltage inputter and the current inputter and based on the corresponding electrical physical quantity of the biosignal.

15 Claims, 5 Drawing Sheets

BIOSIGNAL PROCESSING METHOD AND APPARATUS

CROSS-REFERENCE TO RELATED APPLICATION(S)

This application claims the benefit under 35 USC 119(a) of Korean Patent Application No. 10-2014-0192674, filed on Dec. 29, 2014, in the Korean Intellectual Property Office, the entire disclosure of which is incorporated herein by reference for all purposes.

BACKGROUND

1. Field

The following description relates to a biosignal processing method and a biosignal processing apparatus.

2. Description of Related Art

Various types of biosignal may be measured by a device. For example, a biosignal such as an electrocardiogram (ECG), an electromyogram (EMG), and a photoplethysmogram (PPG) are measured. A circuit to preprocess the ECG is used to measure the ECG, and a circuit to preprocess the EMG is used to measure the EMG. Also, a circuit to preprocess PPG is used to measure the PPG.

When the ECG, the EMG, and the PPG are to be measured by a device, the device includes a circuit to process a corresponding biosignal. When circuits to preprocess corresponding each of the biosignals (the ECG, the EMG, and the PPG) are included in the device, the device is configured to have a relatively large size.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In accordance with an embodiment, there is provided a biosignal processing apparatus, including a signal receiver configured to receive a biosignal having a corresponding electrical physical quantity from a sensor; and a signal processor comprising a voltage inputter and a current inputter, and configured to process the biosignal using one of the voltage inputter and the current inputter and based on the corresponding electrical physical quantity of the biosignal.

The signal processor may be configured to receive the biosignal for each time interval using one of the voltage inputter and the current inputter.

The signal processor may be configured to receive the biosignal using one of the voltage inputter and the current inputter based on a control event occurring in response to a user input.

The signal processor may be configured to receive the biosignal using one of the voltage inputter and the current inputter based on a control signal generated in response to a termination of a time interval for sensing the biosignal.

The current inputter may include a chopper configured to modulate a frequency component of an input current to the current inputter based on the control signal, and configured to change connections between input ends and output ends of the current inputter based on the control signal.

In response to the electrical physical quantity of the biosignal being a current, the signal processor may be configured to receive the biosignal using the current inputter and to receive a reference voltage signal using the voltage inputter.

In response to the electrical physical quantity of the biosignal being a voltage, the signal processor may be configured to receive the biosignal using the voltage inputter, and the current inputter may be configured to control a connection with an electrical element included in the signal processor.

The signal receiver may be configured to receive a current to sense the biosignal.

The signal receiver may include a multiplexer.

Each of the sensors may transmit a biosignal with an electrical physical quantity different from electrical physical quantities of other biosignals.

The signal processor may operate in one of a voltage measuring mode, in which a multiplexer of the signal receiver is connected to the voltage inputter and the current inputter is disconnected, and a current measuring mode, in which the multiplexer of the signal receiver is connected to the signal processor through the current inputter and disconnected from the voltage inputter.

In accordance with another embodiment, there is provided a biosignal processing apparatus, including a signal receiver configured to receive a biosignal having a corresponding electrical physical quantity from sensors; and an analog front-end comprising a voltage inputter and a current inputter, and configured to process the biosignal using one of the voltage inputter and the current inputter and based on the corresponding electrical physical quantity of the biosignal.

The analog front-end may be configured to receive the biosignal for each time interval using one of the voltage inputter and the current inputter.

The analog front-end may be configured to receive the biosignal using one of the voltage inputter and the current inputter based on a control event occurring in response to a user input.

The analog front-end may be configured to receive the biosignal using one of the voltage inputter and the current inputter based on a control signal generated in response to a termination of a time interval for sensing the biosignal.

In response to the electrical physical quantity of the biosignal being a current, the analog front-end may be configured to receive the biosignal using the current inputter and to receive a reference voltage signal using the voltage inputter.

In response to the electrical physical quantity of the biosignal being a voltage, the analog front-end may be configured to receive the biosignal using the voltage inputter, and the current inputter is configured to control a connection with an electrical element included in the analog front-end.

The apparatus may also include a current generator configured to generate a current to sense the biosignal.

In accordance with an embodiment, there is provided a biosignal processing method, including receiving a biosignal output from a sensor; transferring the biosignal to one of a voltage inputter and a current inputter; and processing the biosignal based on an electrical physical quantity of the biosignal received using one of the voltage inputter and the current inputter.

Each biosignal may be received at different time intervals through one of the voltage inputter and the current inputter.

In accordance with an embodiment, there is provided a non-transitory computer readable medium configured to control a processor to perform the method described above.

Other features and aspects will be apparent from the following detailed description, the drawings, and the claims.

Figure 1:
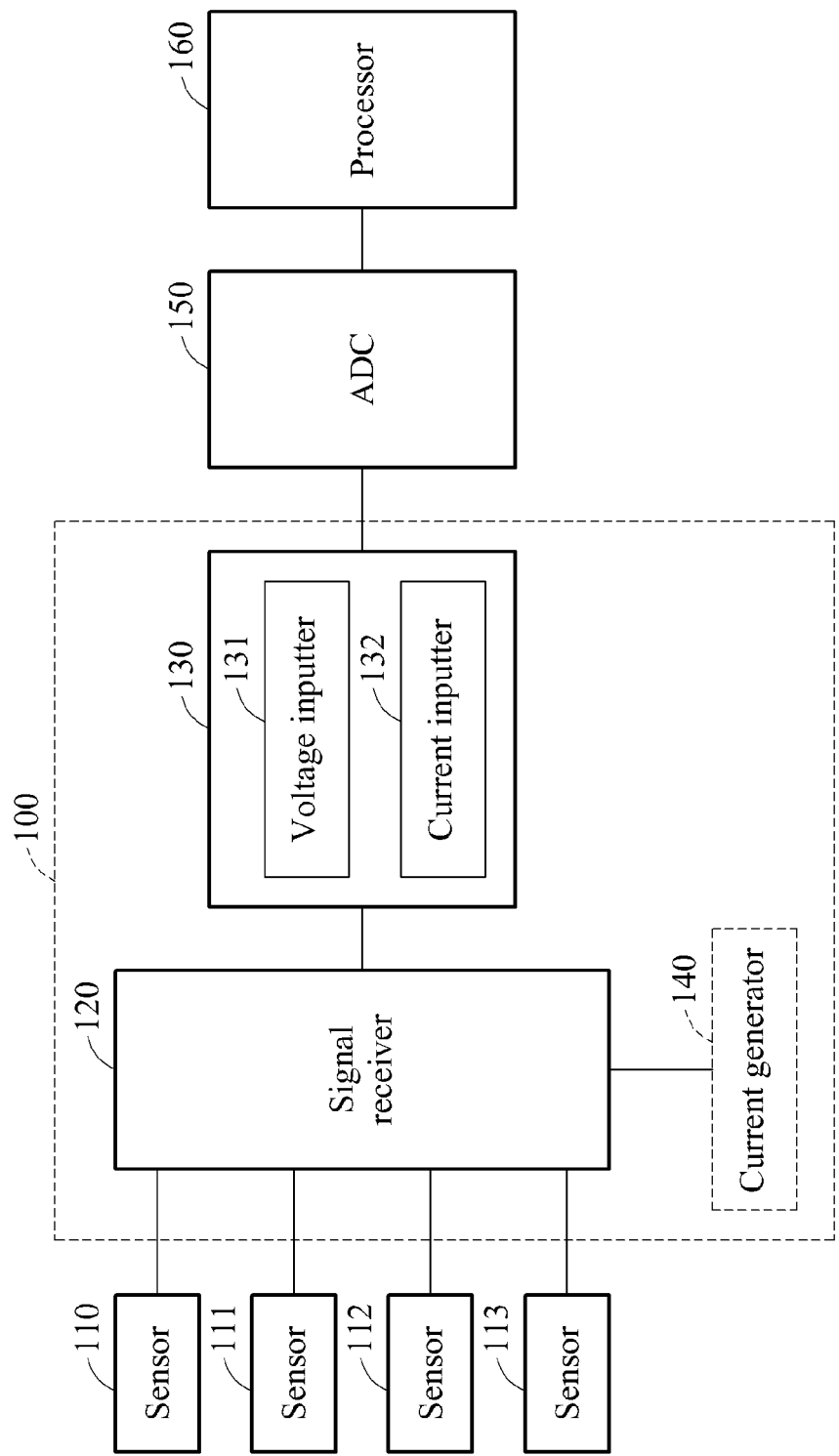
FIG. 1 illustrates an example of a biosignal processing apparatus, in accordance with an embodiment.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Hereinafter, various embodiments will be described in detail with reference to the accompanying drawings.

It should be understood, however, that there is no intent to limit this disclosure to the particular embodiments disclosed. On the contrary, various embodiments are to cover all modifications, equivalents, and alternatives falling within the scope of the embodiments.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "include" and/or "have," when used in this specification, specify the presence of stated features, integers, steps, operations, elements, components or combinations thereof, but do not preclude the presence or addition of one or more other features, integers, steps, operations, elements, components, and/or groups thereof.

Unless otherwise defined, all terms including technical and scientific terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It will be understood that when an element or layer is referred to as being "on" or "connected to" another element or layer, it can be directly on or connected to the other element or layer or through intervening elements or layers may be present. In contrast, when an element is referred to as being "directly on" or "directly connected to" another element or layer, there are no intervening elements or layers present. Like reference numerals refer to like elements throughout. As used herein, the term "and/or" includes any and all combinations of one or more of the associated listed items.

FIG. 1 illustrates a biosignal processing apparatus 100, in accordance with an embodiment.

Referring to FIG. 1, the biosignal processing apparatus 100 includes a signal receiver 120 and a signal processor 130.

The signal receiver 120 receives biosignals from a plurality of sensors, for example, sensors 110 through 113. Each biosignal has a corresponding and different electrical physical quantity from other biosignals. For example, one or more of the sensors transmits a biosignal with a corresponding electrical physical quantity to the signal receiver 120. In one configuration, each of the sensors transmits a signal with a different electrical physical quantity. In another configuration, at least one of the sensors transmits a signal with an electrical physical quantity different from other signals of the other sensors. The sensors include, for example, an electrocardiogram (ECG) sensor, a heart rate measuring sensor, a body temperature measuring sensor, and a bioimpedance measuring sensor.

The ECG sensor senses an ECG signal indicating a heart electrical activity of a user. For example, a signal output by the ECG sensor in response to the sensed ECG signal is an electrical signal, and an electrical physical quantity of the electrical signal is a voltage.

The heart rate measuring sensor includes a light emitter, for example, a light emitting diode (LED) and a light receiver, for example, a photodiode. When the heart rate measuring sensor comes into contact with a body part, for example, a finger, of the user, the light emitter generates a light, and the light receiver receives a light reflected or penetrating based on a change in a blood amount of a blood vessel. In response to the receiving of the light, vessel constriction and dilation are sensed, and the sensed vessel constriction and dilation indicate a heart rate. The light receiver outputs an electrical signal, where an electrical physical quantity of the output electrical signal is a current.

The body temperature measuring sensor includes a thermistor. An increase in a body temperature leads to a change in a resistance value of the thermistor. The body temperature of the user is measured based on the change in the resistance value. For example, when the thermistor comes into contact with a body of the user, the resistance value of the thermistor changes based on the body temperature of the user, and a voltage applied to a resistor of the thermistor changes based on a current flowing through the thermistor. Based on the changed voltage, the body temperature of the user is measured. For example, the body temperature measuring sensor outputs an electrical signal, and an electrical physical quantity of the electrical signal is a voltage.

The bioimpedance measuring sensor senses, for example, a body fat amount of the user. When the bioimpedance measuring sensor comes into contact with the body of the user, a micro-current is applied to the user. Based on the applied micro-current, a bioimpedance of the user is measured. In this example, the bioimpedance measuring sensor outputs a voltage applied to the bioimpedance. In other words, the bioimpedance measuring sensor outputs an electrical signal, and an electrical physical quantity of the output electrical signal is a voltage.

In the foregoing, the plurality of sensors, for example, the sensors 110 through 113, are described as an example and thus, a type of the plurality of sensors is not limited thereto.

The signal receiver 120 receives, from the sensors 110 through 113, a biosignal of which an electrical physical quantity is a voltage or a current. Although the descriptions are provided based on the electrical physical quantity corresponding to the voltage or the current as an example, a type of the electrical physical quantity is not limited thereto. For example, the electrical physical quantity may include an electric power, an amount of the electric power, a frequency, or a number of vibrations.

In an example, the signal receiver 120 includes a multiplexer, referred to as an MUX. The signal receiver 120 or the multiplexer is connected with the sensors 110 through 113, and connected with the signal processor 130. The signal receiver 120 transfers a biosignal sensed by one of the sensors 110 through 113 to one of a voltage inputter 131 and a current inputter 132 in the signal processor 130.

The signal processor 130 includes the voltage inputter 131 and the current inputter 132. The signal processor 130 receives the biosignal output from the signal receiver 120 using one of the voltage inputter 131 and the current inputter 132.

A structural type of an inputter may vary based on a type of the electrical physical quantity of the biosignal. For example, the voltage inputter 131 includes a switch controlled based on a control signal, and receives one of a reference voltage signal and the biosignal using the switch. The current inputter 132 includes a chopper controlled based on a control signal, and controls a connection with an electrical element included in the signal processor 130 using the chopper. The electrical element includes, for example, an active element and a load element such as a resistor.

As an example, when the electrical physical quantity of the biosignal is the voltage, the signal receiver 120 is connected with the voltage inputter 131 using the switch, and the biosignal is input to the voltage inputter 131. The current inputter 132 disconnects the signal receiver 120 from the electrical element included in the signal processor 130 using the chopper. In contrast, when the electrical physical quantity is the current, the signal processor 130 receives the biosignal output from the signal receiver 120 using the current inputter 132. The voltage inputter 131 is connected to a source providing the reference voltage signal using the switch, and receives the reference voltage signal.

As another example, the signal processor 130 operates in one of a voltage measuring mode and a current measuring mode. In the voltage measuring mode of the signal processor 130, the multiplexer of the signal receiver 120 is connected to the voltage inputter 131 and the current inputter 132 is not connected with an electrical element. In the current measuring mode of the signal processor 130, the multiplexer of the signal receiver 120 is connected to the signal processor 130 through the current inputter 132, but is not connected with the voltage inputter 131.

In an example, the signal processor 130 receives the biosignal output from the signal receiver 120 at each predetermined time interval using one of the voltage inputter 131 and the current inputter 132. For example, in a biosignal measurement scenario in which an ECG signal is measured during a first time interval and a heart rate is measured during a second time interval, the signal processor 130 receives the ECG signal measured during the first time interval using the voltage inputter 131. Also, the signal processor 130 receives the heart rate measured during the second time interval, using the current inputter 132.

During the first time interval, the signal receiver 120 receives the ECG signal from the ECG sensor. As described above, the ECG signal has the electrical physical quantity corresponding to the voltage. The voltage inputter 131 is connected with the signal receiver 120, while the current inputter 132 is not connected with the electrical element included in the signal processor 130. The signal receiver 120 transfers the ECG signal to the voltage inputter 131. Although, in one example, current may flow through the current inputter 132, the current is not transferred to the electrical element included in the signal processor 130.

When the first time interval is terminated, a processor 160 generates a control signal requesting or directing a sensing of the heart rate. The control signal is transferred to the heart rate measuring sensor and the signal processor 130. The heart rate measuring sensor senses the heart rate in response to the control signal. As described above, the heart rate sensed at the heart rate measuring sensor has the electrical physical quantity corresponding to the current. In response to the control signal, the signal receiver 120 transfers the sensed heart rate to the current inputter 132 in lieu of the voltage inputter 131. Based on the control signal, the current inputter 132 is connected to the electrical element included in the signal processor 130, and the sensed heart rate flowing into the current inputter 132 is transferred to the signal processor 130. The signal receiver 120 is connected with the voltage inputter 131 during the first time interval, and the voltage inputter 131 is connected to the source providing the reference voltage signal, in lieu of the signal receiver 120, using the switch operating based on the control signal and from the time at which the second time interval starts.

In an example, the signal processor 130 receives the biosignal output from the signal receiver 120 using one of the voltage inputter 131 and the current inputter 132 based on a control event occurring in response to a user input. For example, the user executes a heart rate measuring application, and the processor 160 generates a control event in response to the execution of the heart rate measuring application. The control event is transferred to the heart rate measuring sensor to operate the heart rate measuring sensor. Also, the control event is transferred to the signal processor 130 to control the chopper of the current inputter 132. The heart rate sensed by the heart rate measuring sensor is input to the current inputter 132.

In an example, the signal receiver 120 receives a current signal from a current generator 140 to sense a biosignal. For example, the bioimpedance of a user is measured by applying a micro-current to the user. In the aforementioned biosignal measurement scenario, the bioimpedance is measured during a third time interval. When the second time interval is terminated, the processor 160 generates a control signal to measure the bioimpedance, and the control signal is transferred to a bioimpedance measuring sensor, for example, sensor 112, and the signal processor 130. Also, the control signal is transferred to the current generator 140. In response, the current generator 140 generates the current signal to be applied to the user, based on the control signal. In response to the current signal applied to the user, the bioimpedance measuring sensor measures the bioimpedance.

As described above, the electrical physical quantity of the measured bioimpedance is the voltage. During the second time interval, the voltage inputter 131 is connected with the source providing the reference voltage signal and the switch is switched based on the control signal such that the voltage inputter 131 is connected to the signal receiver 120. The signal receiver 120 transfers the measured bioimpedance to the voltage inputter 131.

In an example, the current generator 140 is included in the biosignal processing apparatus 100. In an alternative configuration, the current generator 140 is disposed externally to the biosignal processing apparatus 100, and the signal receiver 120 receives the current from the current generator 140.

The signal processor 130 processes the biosignal based on the electrical physical quantity of the biosignal output by the signal receiver 120. The signal processor 130 transfers the processed biosignal to an analog-to-digital converter (ADC) 150. Hereinafter, descriptions related to the signal processor 130 processing the biosignal will be provided with reference to FIG. 2.

Figure 2:
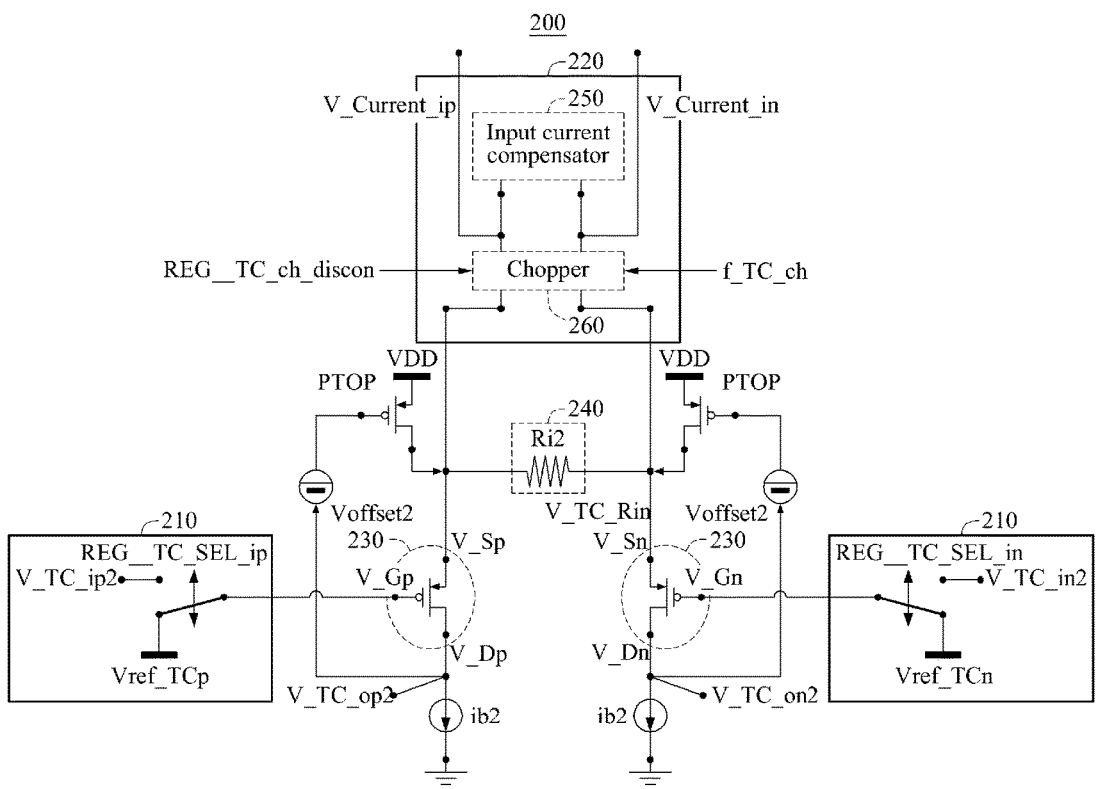
FIG. 2 illustrates an example of a signal processor included in the biosignal processing apparatus, in accordance with an embodiment.

FIG. 2 illustrates a signal processor 200 included in the biosignal processing apparatus, in accordance with an embodiment.

Referring to FIG. 2, the signal processor 200 includes a voltage inputter 210, a current inputter 220, an input element 230, and an electrical element 240.

An operation mode of the signal processor 200 includes a voltage measuring mode and a current measuring mode. The voltage measuring mode corresponds to a case in which a biosignal having an electrical physical quantity of a voltage is input to the voltage inputter 210. The current measuring mode corresponds to a case in which a biosignal having an electrical physical quantity of a current is applied to the current inputter 220.

In the voltage measuring mode, the voltage inputter 210 selects an input voltage from a plurality of input voltages. The plurality of input voltages includes a target voltage to be measured and a reference voltage set in advance. The target voltage includes, for example, an ECG signal measured by an ECG sensor, a body temperature measured by a body temperature measuring sensor, and a bioimpedance measured by a bioimpedance measuring sensor. The target voltage is a biosignal having the electrical physical quantity, for example, the voltage, described with reference to FIG. 1. In FIG. 2, a differential voltage of V_TC_ip2 and V_TC_in2 indicates the target voltage, and Vref_TCp and Vref_TCn indicate the reference voltage. Vref_TCp and Vref_TCn have the same voltage level or different voltage levels from one another. Also, Vref_TCp and Vref_TCn have fixed voltage levels or varying voltage levels over time.

The voltage inputter 210 is connected to the input element 230. The voltage inputter 210 selects an input voltage to be applied to the input element 230 using a switch. A control signal is used to determine the input voltage applied to the input element 230. In FIG. 2, REG_TC_SEL_ip and REG_TC_SEL_in may indicate a control signal used to control a switching operation of the switch. The input element 230 generates a current in response to the input voltage selected by the voltage inputter 210 in the voltage measuring mode. For example, the input element 230 is a transistor as a transconductance element, and includes a plurality of transconductance elements. The input element 230 converts the input voltage into a current.

The current inputter 220 controls an inflow of an input current based on an operation of the voltage inputter 210. For example, when the signal processor 200 operates in the voltage measuring mode, the current inputter 220 blocks the inflow of the input current.

In the current measuring mode, an input current to be measured is an input to the signal processor 200 using the current inputter 220. For example, the heart rate sensed by the heart rate sensor is input to the signal processor 200 as the input current. The input current corresponds to the biosignal having the electrical physical quantity, for example, the current, described with reference to FIG. 1. The current inputter 220 controls the inflow of the input current using the switch controlled based on the control signal. In FIG. 2, a differential current of V_Current_ip and V_Current_in is indicative of the input current to be measured, and REG_TC_ch_discon is indicative of the control signal used to control the switching operation of the chopper 260 in the current inputter 220.

The electrical element 240 is coupled with the current inputter 220 and the input element 230. For example, an output end of the current inputter 220 is connected to both ends of the electrical element 240, and one end of the input element 230 is connected to the electrical element 240. In this example, "being coupled" includes an embodiment in which the electrical element 240 is directly connected with the current inputter 220 and the input element 230, or an embodiment in which the electrical element 240 is affected by the current inputter 220 and the input element 230 through another element. In one configuration, the electrical element 240 is a resistor. A current flowing through the input element 230 or a current flowing through the current inputter 220 affects a current flowing through both ends of the electrical element 240 to be changed.

In an example, the current inputter 220 further includes an input current compensator 250 to adjust a level of the input current. The input current compensator 250 generates a compensation current to adjust the level of the input current. When the level of the input current is beyond an operable range of the signal processor 200, the input current compensator 250 outputs an offset current such that the level of the input current is incorporated in the operable range of the signal processor 200.

As an example, the input current compensator 250 outputs a compensation current to decrease a direct current (DC) level of the input current to be within a preset range. To decrease the DC level of the input current, the input current compensator 250 outputs a compensation current having a negative DC level, for example, −3 milliamperes (mA). The level of the input current is adjusted by adding the compensation current output from the input current compensator 250 to the input current.

In an example, the input current compensator 250 operates in a manual adjustment mode or an automatic adjustment mode. In the manual adjustment mode, the input current compensator 250 manually adjusts the level of the input current under a control of a user. In the automatic adjustment mode, the input current compensator 250 adaptively adjusts the level of the input current based on an output signal of the signal processor 200. For example, in the automatic adjustment mode, the input current compensator 250 extracts a signal of a low frequency band from the output signal of the signal processor 200, and determines whether the level of the input current is to be adjusted based on a level of the extracted signal of the low frequency band. Based on a result of the determining, the input current compensator 250 determines a level of the compensation current to adjust the level of the input current and output the compensation current corresponding to the determined level, to then adjust the level of the input current flowing through the signal processor 200.

In the automatic adjustment mode, the signal processor 200 further includes an input current compensation controller (not shown) configured to generate a control signal to control the input current compensator 250. The input current compensation controller controls the level of the compensation current output from the input current compensator 250 based on the output signal o the signal processor 200. In an example, the signal processor 200 further includes a low pass filter (not shown) configured to output the signal of the low frequency band in response to the output signal of the signal processor 200. The signal processor 200 also includes a comparator (not shown) configured to compare a level of an output signal of the low pass filter to a level of a preset reference signal and output a result of the comparing to the input current compensation controller. Based on the result of the comparator, the input current compensation controller generates the control signal to control the input current compensator 250.

In an example, the chopper 260 included in the current inputter 220 modulates a frequency component of the input current based on the control signal. The chopper 260 changes connections between input ends and output ends of the current inputter 320 based on the control signal. When the chopper 260 modulates the frequency component of the input current, low frequency noise, 1/f noise, or flicker noise is reduced. For example, when the chopper 260 modulates the input current into a signal of a high frequency band, the low frequency noise occurring in the signal of the low frequency band is reduced. When the chopper 260 does not perform a signal modulating operation, the chopper 260 operates as a switch allowing and disallowing the inflow of the input current.

Hereinafter, an operation of the signal processor 200 in the voltage measuring mode and an operation of the signal processor 200 in the current measuring mode will be explained in detail with reference to the following descriptions.

The operation of the signal processor 200 in the voltage measuring mode will be described as below.

In the voltage measuring mode, the signal processor 200 blocks the inflow of the input current, and selects a target voltage as an input voltage.

The voltage inputter 210 applies the input voltage to the input element 230. For example, the voltage inputter 210 applies input voltages V_TC_ip2 and V_TC_in2 to gate nodes V_Gp and V_Gn of the input element 230, respectively. The input voltages V_TC_ip2 and V_TC_in2 are in a differential input relationship. In response to a control signal REG_TC_SEL_ip having a logic value High (H), the input voltage V_TC_ip2 are applied to the gate node V_Gp. In response to a control signal REG_TC_SEL_in having a logic value H, the input voltage V_TC_in2 is applied to the gate node V_Gn. Through this, the input voltage is input to the signal processor 200.

The input voltages V_TC_ip2 and V_TC_in2 having the differential input relationship may affect the current flowing through both ends of the electrical element 240.

In response to the applied input voltage, the input element 230 generates a current flowing from a source node V_Sp to a drain node V_Dp, and a current flowing from a source node V_Sn to a drain node V_Dn. The drain node V_Dp is connected to an output node V_TC_op2 of the signal processor 200, and the drain node V_Dn is connected to an output node V_TC_on2 of the signal processor 200.

The current inputter 220 blocks the input current flowing into the signal processor 200. For example, in response to a control signal REG_TC_ch_discon having a logic value H, switches included in the chopper 260 of the current inputter 220 are disconnected from one another and; thus, an input end of the current inputter 220 are not connected to the electrical element 240.

The operation of the signal processor 200 in the current measuring mode will be described as below.

In the current measuring mode, the signal processor 200 allows or provides the input of the input current, and selects the preset reference voltage as the input voltage in lieu of the voltage to be measured.

The voltage inputter 210 applies a reference voltage having a fixed voltage level to the input element 230. For example, in response to the control signal REG_TC_SEL_ip having a logic value Low (L), the voltage inputter 210 applies a reference voltage Vref_TCp having a fixed voltage level to the gate node V_Gp. Further, in response to the control signal having the logic value Low (L), the voltage inputter 210 applies a reference voltage Vref_TCn having a fixed voltage level to the gate node V_Gn.

Because a fixed current ib2 flows through the input element 230, a constant voltage level is maintained in the source nodes V_Sp and V_Sn of the input element 230. By adjusting a voltage level of the reference voltage Vref_TCp, a desired voltage is generated in the source node V_Sp. By adjusting a voltage level of the reference voltage Vref_TCn, a desired voltage is generated in the source node V_Sn.

The current inputter 220 applies the input current to be measured to the signal processor 200. For example, the current inputter 220 applies an input current V_Current_ip or V_Current_in to be measured. The input currents V_Current_ip and V_Current_in are in a differential input relationship. In response to the control signal REG_TC_ch_discon having the logic value L, the switches included in the chopper 260 are connected to one another such that the input end of the current inputter 220 is connected to the electrical element 240 through the chopper 260.

The input currents V_Current_ip and V_Current_in having the differential input relationship may affect the current flowing through both ends of the electrical element 240.

Figure 3:
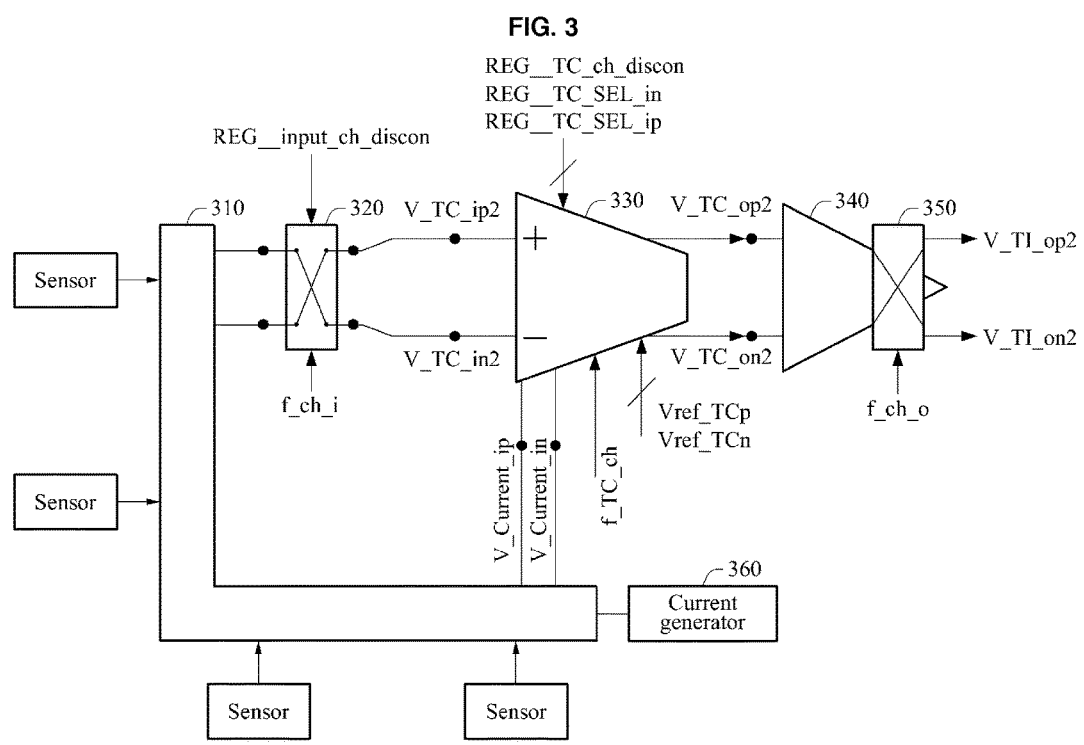
FIG. 3 illustrates an example of operating the biosignal processing apparatus, in accordance with an embodiment.

FIG. 3 illustrates an example of operating the biosignal processing apparatus, in accordance with an embodiment.

Referring to FIG. 3, the biosignal processing apparatus includes a signal receiver 310 and a first signal processor 330. Also, the biosignal processing apparatus further includes an input chopper 320 and a second signal processor 340.

The signal receiver 310 is connected to sensors. For example, the signal receiver 310 is connected with at least one of an ECG sensor, a heart rate measuring sensor, a body temperature measuring sensor, and a bioimpedance measuring sensor. Also, the signal receiver 310 is connected with at least one of the sensors to sense a biosignal. The signal receiver 310 is connected to a current generator 360 configured to generate a current used to sense a biosignal. The signal receiver 310 includes a multiplexer.

A control signal is generated based on a biosignal measurement scenario. The first signal processor 330 determines an operation mode based on the control signal. For example, the first signal processor 330 operates in one of a voltage measuring mode and a current measuring mode.

In the biosignal measurement scenario, a first time interval is a time interval to sense an ECG signal. In one illustrative example, the ECG signal sensed by the ECG sensor is an electrical physical quantity corresponding to a voltage. Based on control signals REG_TC_SEL_in, REG_TC_SEL_ip, and REG_TC_ch_discon, the first signal processor 330 operates in the voltage measuring mode. The signal receiver 310 is used to input the ECG signal to the input chopper 320. The ECG signal is modulated by the input chopper 320.

The first signal processor 330 receives ECG signals V_TC_in2 and V_TC_ip2 passing through the input chopper 320. The first signal processor 330 disconnects an electrical element included in the first signal processor 330 from an input end receiving a biosignal having an electrical physical quantity corresponding to a current based on the control signal REG_TC_ch_discon.

A second time interval provided subsequently to the first time interval is a time interval to sense a heart rate. The heart rate sensed by the heart rate measuring sensor is an electrical physical quantity corresponding to the current. Based on the control signals REG_TC_SEL_in, REG_TC_SEL_ip, and REG_TC_ch_discon, the first signal processor 330 operates in the current measuring mode.

The first signal processor 330 receives reference voltage signals Vref_TCp and Vref_TCn based on the control signals REG_TC_SEL_in and REG_TC_SEL_ip. The input chopper 320 does not operate based on the control signal REG_input_ch_discon. The first signal processor 330 is not connected to the input end receiving the electrical physical quantity corresponding to the voltage based on the control signal REG_input_ch_discon.

During the first time interval, the electrical element included in the first signal processor 330 is disconnected from the input end receiving the heart rate signal. During the second time interval, the electrical element is connected to the input end receiving the heart rate signal, and the first signal processor 330 receives heart rate signals V_Current_ip and V_Current_in. For example, a third time interval provided subsequently to the second time interval is a time interval to sense a body temperature. A biosignal output from the body temperature measuring sensor is an electrical physical quantity corresponding to the voltage. The first signal processor 330 operates in the voltage measuring mode based on the control signals REG_TC_SEL_in, REG_TC_SEL_ip, and REG_TC_ch_discon.

During the second time interval, the first signal processor 330 is not connected with the input end receiving the biosignal having the electrical physical quantity corresponding to the voltage. Based on the control signals REG_TC_SEL_in and REG_TC_SEL_ip, the first signal processor 330 is connected to the input end receiving the biosignal having the electrical physical quantity corresponding to the voltage. Further, the first signal processor 330 does not receive the reference voltage signals Vref_TCp and Vref_TCn.

The first signal processor 330 disconnects the electrical element included in the processor 330 from the input end receiving the biosignal, which has the electrical physical quantity corresponding to the current based on the control signal REG_TC_ch_discon.

During each time interval of the biosignal measurement scenario, the second signal processor 340 generates output voltages V_TI_op2 and V_TI_on2 based on the current output from the first signal processor 330.

The second signal processor 340 includes an output chopper 350 to demodulate a signal of a high frequency band, into which the heart rate signal is modulated by the input chopper 320, into a signal of a low frequency band. A control signal f_ch_o is used to control a connection of each switch included in the output chopper 350. In an example, the control signal f_ch_o applied to the output chopper 350 has the same signal waveform as that of a control signal f_ch_i applied to the input chopper 320.

Figure 4:
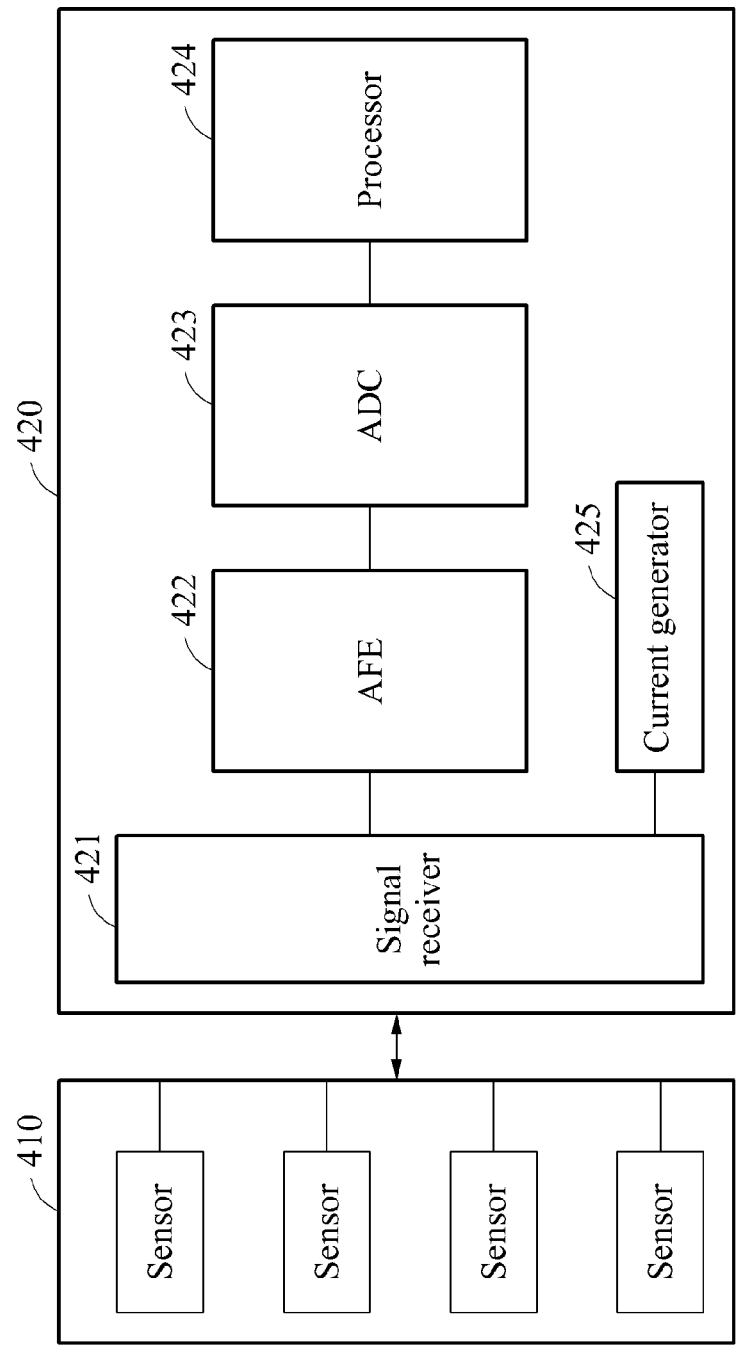
FIG. 4 illustrates another example of a biosignal processing apparatus, in accordance with an embodiment.

FIG. 4 illustrates another example of a biosignal processing apparatus, in accordance with an embodiment. The input chopper 320, the first signal processor 330, the second signal processor 340, and the output chopper 350 of FIG. 3 may correspond to an analog front-end 422 of FIG. 4.

The biosignal processing apparatus includes a main module 420. The main module 420 is connected with a sub-module 410 including a plurality of sensors. In one configuration, an architecture or form of the sub-module 410 may be modified or varied based on a manner in which the sub-module 410 is worn on a body of a user or a wearing method on the body. The sub-module 410 is provided in, for example, a watch-type, a garment-type, and a chest belt-type. The main module 420 is attachable to and detachable from the sub-module 410. The sensors include, for example, an ECG sensor, a heart rate measuring sensor, a body temperature sensor, and a bioimpedance sensor. Hereinafter, as an illustrative example, the following descriptions will be provided based on the main module 420 connected with the sub-module 410.

The main module 420 includes a signal receiver 421 to receive a biosignal having a different electrical physical quantity from each of the sensors. In accordance with an alternative configuration, at least one biosignal received from the sensors has a different electrical physical quantity from the other biosignals. For example, an ECG signal sensed by the ECG sensor, a body temperature sensed by the body temperature measuring sensor, and a bioimpedance sensed by the bioimpedance measuring sensor have an electrical physical quantity corresponding to a voltage. A heart rate sensed by the heart rate measuring sensor has an electrical physical quantity corresponding to a current. In an example, the signal receiver 421 includes a multiplexer including at least one input end and at least one output end. The at least one input end of the multiplexer is connected to the sub-module 410, and the at least one output end of the multiplexer is connected to the analog front-end 422.

The analog front-end 422 includes a voltage inputter (not shown) and a current inputter (not shown). Hereinafter, the analog front-end (AFE) 422 receives a biosignal output from the signal processor 421 using one of the voltage inputter and the current inputter. For example, the AFE 422 uses the voltage inputter to receive the biosignal having the electrical physical quantity corresponding to the voltage, and uses the current inputter to receive the electrical physical quantity corresponding to the current.

When the electrical physical quantity of the biosignal is the voltage, the current inputter of the AFE 422 controls a connection to an electrical element included in the AFE 422. For example, the current inputter includes a chopper controlled based on a control signal, and the chopper disconnects the current inputter from the electrical element.

When the electrical physical quantity of the biosignal is the current, the AFE 422 receives a reference voltage signal using the voltage inputter. The multiplexer is not connected to the voltage inputter, and a source providing the reference voltage signal is connected to the voltage inputter.

The AFE 422 receives the biosignal output from the signal receiver 421 for each predetermined time interval using one of the voltage inputter and the current inputter. For example, during a first time interval, the AFE 422 receives an ECG signal using the voltage inputter. During the first time interval, the voltage inputter of the AFE 422 is connected to the multiplexer while the current inputter is disconnected from an electrical element in the AFE 422.

When the first time interval is terminated, a processor 424 generates a control signal to sense a heart rate in response to a start of a second time interval. The control signal is used to operate the heart rate measuring sensor and control the AFE 422. For example, during the first time interval, the current inputter is disconnected from the electrical element in the AFE 422, and the current inputter is connected to the electrical element based on the control signal in response to the start of the second time interval. Also, the voltage inputter is connected with the multiplexer during the first time interval, and the voltage inputter is disconnected from the multiplexer based on the control signal in response to the start of the second time interval. The voltage inputter is connected to the source providing the reference voltage signal, and the AFE 422 receives the reference voltage signal using the voltage inputter.

When the second time interval is terminated, the processor 424 generates a control signal for measuring a body temperature in response to a start of the third time interval. The control signal is used to operate the body temperature measuring sensor and the current generator 425. The body temperature sensor includes a thermistor. A resistance value of the thermistor varies based on a change in temperature. To measure the varying resistance value, a current, for example, a DC, generated by the current generator 425 is applied to the thermistor and a voltage value changes based on the varying resistance value. The body temperature measuring sensor transfers the change in the voltage value to the signal receiver 421.

During the second time interval, the current inputter is connected to the electrical element included in the AFE 422, and, in response to the start of the third time interval, the current inputter is disconnected from the electrical element included in the AFE 422 based on the control signal. Also, during the second time interval, the current inputter is connected to the source providing the reference voltage signal in lieu of the signal receiver 421. In response to the start of the third time interval, the voltage inputter is connected to the signal receiver 421 based on the control signal, and the AFE 422 receives the change in the voltage value using the voltage inputter.

The aforementioned first time interval, second time interval, and third time interval are connected to one another. For example, when the first time interval is terminated, the second time interval starts. Also, when the second time interval is terminated, the third time interval starts. As an example, in a 60 minute duration, the first time interval continues for the first 20 minutes, the second time interval continues for subsequent 20 minutes and then, the third time interval continues for 20 minutes. When each time interval is connected in sequence, the control signal to sense the heart rate is generated simultaneously as the first time interval terminates, and the control signal to measure the body temperature is generated simultaneously as the second time interval terminates.

Also, the second time interval does not start simultaneously with the termination of the first time interval. For example, the first time interval starts at 2:00 p.m. and terminates at 3:00 p.m. today, and the second time interval starts at 2:00 p.m. and terminates at 3:00 p.m. tomorrow. A user sets a time interval to sense and process the biosignal. In accordance with an alternative configuration, the main module 420 is configured to include a pre-defined time interval, which a user may adjust or reset based on a patient's health condition, including age.

In an example, based on a control event occurring in response to a user input, the AFE 422 receives the biosignal output from the signal receiver 421 using one of the voltage inputter and the current inputter. For example, the user executes a bioimpedance measurement application to verify an amount of body fat. In response to the executed bioimpedance measurement application, the processor 424 generates a control event to measure the bioimpedance. The bioimpedance measuring sensor outputs a voltage value corresponding to the bioimpedance to the signal receiver 421. The control event is transferred to the AFE 422, and the AFE 422 receives the voltage value output by the signal receiver 421 using the voltage inputter.

The AFE 422 processes the biosignal based on the electrical physical quantity of the biosignal. As an example, when the electrical physical quantity of the biosignal is the voltage, the biosignal is transferred to a gate node of a transconductance element included in the AFE 422. The voltage is applied to the gate node of the transconductance element. Based on the applied voltage, the AFE 422 controls a current flowing from a source node to a drain node in the transconductance element. The current output from the drain node is transferred to a transimpedance element. The transimpedance element converts the current into a voltage, and the voltage is transferred to an ADC 423.

As another example, when the electrical physical quantity of the biosignal is the current, the reference voltage signal is transferred to the gate node of the transconductance element in the AFE 422. A reference voltage having a constant level is applied to the gate node of the transconductance element. A constant voltage is applied to the gate node of the transconductance element. The biosignal received by the gate node has an electrical attribute of a current, and is transferred to the transimpedance element through the source node and the drain node of the transconductance element. The transimpedance element converts the current into a voltage, and transfers the voltage to the ADC 423.

Because the descriptions provided with reference to FIGS. 1 through 3 are also applicable here, repeated descriptions with respect to FIG. 4 will be omitted for increased clarity and conciseness.

Figure 5:
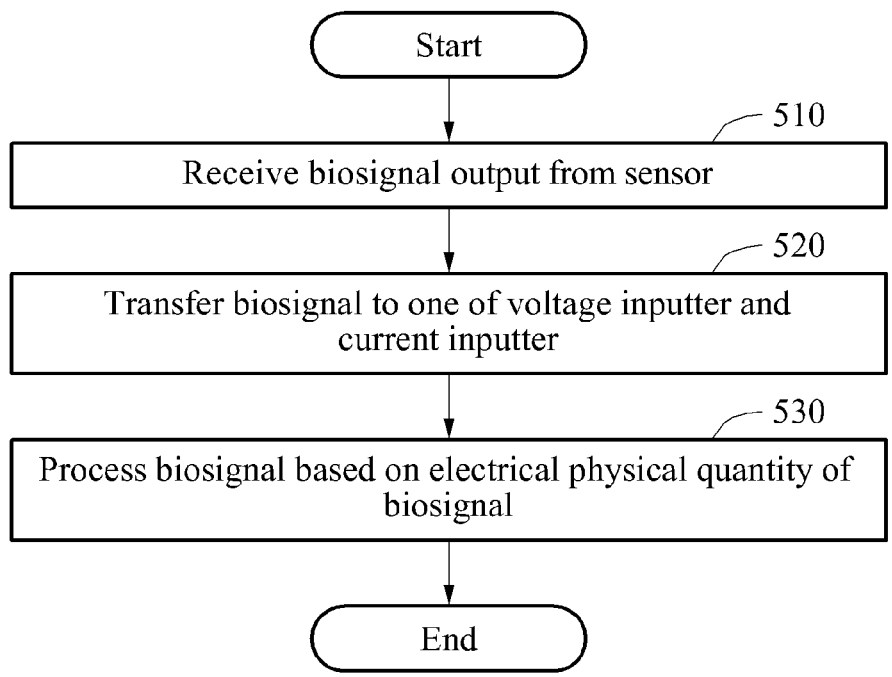
FIG. 5 illustrates an example of a biosignal processing method, in accordance with an embodiment.

FIG. 5 illustrates an example of a biosignal processing method, in accordance with an embodiment.

The biosignal processing method is performed by the biosignal processing apparatus as described in the various embodiments presented above.

In operation 510, the biosignal processing apparatus receives a biosignal output from a sensor.

In operation 520, the biosignal processing apparatus transfers the biosignal to one of a voltage inputter and a current inputter.

In operation 530, the biosignal processing apparatus processes the biosignal received through one of the voltage inputter and the current inputter based on an electrical physical quantity of the biosignal.

Because the descriptions provided with reference to FIGS. 1 through 4 are also applicable here, repeated descriptions with respect to FIG. 5 will be omitted for increased clarity and conciseness.

A biosignal output from a plurality of sensors is an electrical signal, and the electrical signal output from each of the sensors is processed by a different AFE. In response to each of the sensors needing a corresponding AFE, and in response to the plurality of sensors being embedded in a wearable device, the wearable device includes AFEs corresponding to a number of the sensors and, thus, in one example, the wearable device have a relatively large size.

In order to avoid the wearable device from having a relatively large size, in accordance with an embodiment, various signals output from the plurality of sensors are processed by a single AFE. The biosignal processing apparatus, in accordance with an embodiment, processes various types of biosignals and, thus, is provided in a compact or reduced size. Also, in a scenario of measuring a plurality of biosignals, when each of the biosignals has a relatively short measurement interval, a similar or identical result to a result obtained by measuring each of the biosignals simultaneously.

The apparatuses, receivers, converters, inputters, outputters, an analog front-end, generators, units, modules, devices, and other components illustrated in FIGS. 1-4 that perform the operations described herein with respect to FIG. 5 are implemented by hardware components. Examples of hardware components include controllers, sensors, generators, drivers, and any other electronic components known to one of ordinary skill in the art. In one example, the hardware components are implemented by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIG. 5. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The method illustrated in FIG. 5 that perform the operations described herein with respect to FIGS. 1-4 are performed by a processor or a computer as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A biosignal processing apparatus, comprising:
a signal receiver configured to receive a voltage signal and a current signal, transfer the voltage signal to a voltage inputter, and transfer the current signal to a current inputter, wherein the voltage signal indicates a biosignal of which an electrical physical quantity is a voltage and the current signal indicates a biosignal of which an electrical physical quantity is a current; and
a signal processor configured to receive the voltage signal using the voltage inputter and the current signal using the current inputter,
wherein when the signal processor receives the voltage signal, the voltage inputter applies the voltage biosignal to a first electrical element of the signal processor as an input voltage and the current inputter is disconnected from a second electrical element of the signal processor, and
when the signal processor receives the current signal, the voltage inputter applies a reference voltage to the first electrical element as the input voltage, and the current inputter outputs the current signal to the second electrical element as an input current.

2. The apparatus of claim 1, wherein the signal processor is configured to receive the voltage signal or the current signal for each time interval using one of the voltage inputter and the current inputter.

3. The apparatus of claim 1, wherein the signal processor is configured to receive the voltage signal or the current signal using one of the voltage inputter and the current inputter based on a control event occurring in response to a user input.

4. The apparatus of claim 1, wherein the signal processor is configured to receive the voltage signal or the current signal using one of the voltage inputter and the current inputter based on a control signal generated in response to a termination of a time interval for sensing the biosignal.

5. The apparatus of claim 4, wherein the current inputter comprises a chopper configured to modulate a frequency component of an current signal to the current inputter based on the control signal, and configured to change connections between input ends and output ends of the current inputter based on the control signal.

6. The apparatus of claim 1, wherein the signal receiver is configured to receive a current to sense a biosignal.

7. The apparatus of claim 1, wherein the signal processor operates in one of a voltage measuring mode, in which a multiplexer of the signal receiver is connected to the voltage inputter and the current inputter is disconnected, and a current measuring mode, in which the multiplexer of the signal receiver is connected to the signal processor through the current inputter and disconnected from the voltage inputter.

8. A biosignal processing apparatus, comprising:
a signal receiver configured to receive a voltage signal and a current signal, transfer the voltage signal to a voltage inputter, and transfer the current signal to a current inputter, wherein the voltage signal indicates a biosignal of which an electrical physical quantity is a voltage and the current signal indicates a biosignal of which an electrical physical quantity is a current; and
an analog front-end configured to receive the voltage signal using the voltage inputter and the current signal using the current inputter, wherein
when the analog front-end receives the voltage signal, the voltage inputter applies the voltage biosignal to a first electrical element of the analog front-end as an input voltage and the current inputter is disconnected from a second electrical element of the analog front-end, and
when the analog front-end receives the current signal, the voltage inputter applies a reference voltage to the first electrical element as the input voltage, and the current inputter outputs the current signal to the second electrical element as an input current.

9. The apparatus of claim 8, wherein the analog front-end is configured to receive the voltage signal or the current signal for each time interval using one of the voltage inputter and the current inputter.

10. The apparatus of claim 8, wherein the analog front-end is configured to receive the voltage signal or the current signal using one of the voltage inputter and the current inputter based on a control event occurring in response to a user input.

11. The apparatus of claim 8, wherein the analog front-end is configured to receive the voltage signal or the current signal using one of the voltage inputter and the current inputter based on a control signal generated in response to a termination of a time interval for sensing the biosignal.

12. The apparatus of claim 8, further comprising:
a current generator configured to generate a current to sense a biosignal.

13. A biosignal processing method, comprising:
receiving a voltage signal using a voltage inputter or a current signal using a current inputter, wherein the voltage signal indicates a biosignal of which an electrical physical quantity is a voltage and the current signal indicates a biosignal of which an electrical physical quantity is a current;
when receiving the voltage signal, applying the voltage biosignal to a first electrical element of a signal processor as an input voltage and disconnecting the current inputter from a second electrical element of the signal processor, and
when receiving the current signal, applying the reference voltage to the first electrical element as an input voltage, and outputting the current signal to the second electrical element as an input current.

14. The method of claim 13, wherein voltage signal or the current signal is received at different time intervals through one of the voltage inputter and the current inputter.

15. A non-transitory computer readable medium configured to control a processor to perform the method of claim 13.

* * * * *